United States Patent [19]

Sams

[11] Patent Number: 4,865,591
[45] Date of Patent: Sep. 12, 1989

[54] MEASURED DOSE DISPENSING DEVICE
[75] Inventor: Bernard Sams, London, England
[73] Assignee: Hypoguard (UK) Limited, Woodbridge, England
[21] Appl. No.: 205,198
[22] Filed: Jun. 10, 1988

Related U.S. Application Data

[63] Continuation-in-part of Ser. No. 81,241, Aug. 4, 1987, abandoned.

[30] Foreign Application Priority Data

Jun. 12, 1987 [GB] United Kingdom ............... 8713810

[51] Int. Cl.⁴ .......................................... A61M 5/315
[52] U.S. Cl. ................................... 604/186; 604/208; 604/209; 604/211; 222/287; 222/391
[58] Field of Search .............. 604/186, 208, 209, 210, 604/211; 222/43, 309, 325, 326, 327, 391, 287

[56] References Cited

U.S. PATENT DOCUMENTS

| | | | |
|---|---|---|---|
| 1,997,129 | 4/1935 | Taylor et al. | 221/47 |
| 2,605,763 | 8/1952 | Smoot | 128/173 |
| 2,695,023 | 11/1954 | Brown | 128/218 |
| 2,718,299 | 9/1955 | Atwater et al. | 206/42 |
| 3,141,583 | 7/1964 | Mapel et al. | 222/391 X |
| 3,293,749 | 12/1966 | George et al. | 222/391 X |
| 3,348,545 | 10/1967 | Sarnoff et al. | 128/218 |
| 3,517,668 | 6/1970 | Brickson | 128/218 |
| 3,894,663 | 7/1975 | Carhart et al. | 222/309 |
| 3,977,574 | 8/1976 | Thomas | 222/391 |
| 4,022,207 | 5/1977 | Citrin | 128/218 C |
| 4,099,548 | 7/1978 | Sturm et al. | 141/27 |
| 4,395,921 | 8/1983 | Oppenlander | 73/864.18 |
| 4,413,760 | 11/1983 | Paton | 222/309 |
| 4,415,101 | 11/1983 | Shapiro et al. | 222/288 |
| 4,457,712 | 7/1984 | Dragan | 433/90 |
| 4,470,317 | 9/1984 | Sabloewski et al. | 73/864.16 |
| 4,475,905 | 10/1984 | Himmelstrup | 604/208 |
| 4,498,904 | 2/1985 | Turner et al. | 604/211 |
| 4,526,294 | 7/1985 | Hirschmann et al. | 222/407 |
| 4,710,172 | 12/1987 | Jacklich et al. | 604/118 |

FOREIGN PATENT DOCUMENTS

| | | | |
|---|---|---|---|
| 245198 | 5/1963 | Australia | 222/391 |
| 0037696 | 10/1981 | European Pat. Off. | |
| 0143895 | 6/1985 | European Pat. Off. | |
| 730971 | 1/1943 | Fed. Rep. of Germany | |
| 1149735 | 7/1957 | France | |
| 1170312 | 9/1958 | France | |
| 1445659 | 6/1966 | France | |
| 22140 | 10/1961 | German Democratic Rep. | 222/391 |
| 8502546 | 6/1985 | PCT Int'l Appl. | |
| 293302 | 9/1953 | Switzerland | |
| 1225495 | 3/1971 | United Kingdom | |
| 2109690 | 6/1983 | United Kingdom | |

Primary Examiner—Martin P. Schwadron
Assistant Examiner—Allen J. Flanigan
Attorney, Agent, or Firm—Willian Brinks Olds Hofer Gilson & Lione

[57] ABSTRACT

The present invention relates to a device for dispensing a fluid from a container by means of the axial movement of a piston within the container under the influence of a plunger moved by the device, which device is adapted to receive the container on its forward end and to move the plunger axially forward towards or within the container so as to dispense a selected amount of fluid from the container upon each actuation of the device, characterized in that the device comprises:

i. a disengageable drive mechanism adapted to be reciprocated axially of the device and adapted to positively engage the plunger whereby the plunger can be moved axially forward by the drive mechanism and to be disengaged from the plunger to permit relative axial movement between the drive mechanism and the plunger;

ii. a disengagement means for selectively engaging or disengaging the drive means from the plunger;

iii. an actuating means, which may be integral with or separate from the disengagement means, for actuating the disengagement means, which actuation means requires a positive operation from a user of the device to engage and/or disengage the drive mechanism from the plunger; and iv. means for selecting the extent of travel of the drive mechanism so as to control the extent of axial movement of the plunger upon actuation of the device.

The invention also provides a device of the invention in association with a container of the fluid to be dispensed.

19 Claims, 4 Drawing Sheets

MEASURED DOSE DISPENSING DEVICE

CROSS-REFERENCE TO RELATED APPLICATION

This application is a continuation-in-part of copending U.S. patent application Ser. No. 07/081,241, filed Aug. 4, 1987 now abandoned. The entire text of this application Ser. No. 07/081,241 is hereby incorporated by reference.

The present invention relates to a measured dose dispensing device.

BACKGROUND TO THE INVENTION

Patients suffering from diabetes often have to inject themselves with frequent doses of insulin and this can be done using a conventional syringe. However, the patients often also suffer from side effects of their illness and are not capable of accurately controlling the operation of such a syringe. It is therefore desirable that they should be provided with means for automatically administering an accurately controlled dosage. However, the dosage required by different patients can vary over quite wide ranges, from for example 2 units of insulin per dose to 30 or more units, and it is necessary to ensure that any device is capable of selecting a range of dosages simply and accurately.

Many forms of dispensing device use a pawl and ratchet mechanism to connect a push button or trigger operated by the user to a plunger driving a piston in the barrel of the syringe or a cartridge carried by the device. This achieves a positive drive on the forward stroke, but allows the button or trigger to be retracted, for example under the bias of a return spring, with the pawl riding over the teeth of the ratchet, in readiness for the next actuation of the device. The drive between the pawl and the ratchet is thus never fully disengaged. Typical of such devices are those described for example in U.S. Pat. Nos. 1997129, 2605763, 2718299, 3517668, 3894663, 3977574, 4022207, 4099549, 4415101, 4457712 and 4470317; French Patent Specifications Nos. 1445659, 1170312 and 1149735; and German Patent Specification No. 730971.

Where any provision is made for selecting the volume of fluid to be dispensed, this is usually by way of stops limiting the depression of the push button or trigger operating the device.

European Patent No. 0037696 describes a device in which positive drive between the plunger and the push button is achieved by having ratchet teeth along the length of the plunger into which engage the co-operating teeth of a spring loaded pawl member carried on an axially operated push member extending through the rear end of the device. A stop engaging in a slot in the push member limits the extent of travel of the push member and the volume of fluid to be dispensed is selected by withdrawing the push member the required distance from the forward extreme of its travel with the pawl riding over the teeth of the ratchet. The dose is administered by depressing the push member which carries the plunger with it. Once the plunger has reached the forward extreme of its travel and the container has been emptied, the pawl automatically disengages from the plunger to allow the plunger to be fully retracted to permit a new container to be fitted to the device.

In the above forms of device, an essential feature of the design is that the pawl is free to ride over the teeth of a ratchet as the pawl is retracted and the drive is thus not fully disconnected from the ratchet so as to be ready for driving the ratchet forward in the next delivery stroke of the device. Firstly, this does not permit a user to correct any error in setting the extent of retraction where this is used to set the amount of fluid to be dispensed. As a result, if too large a retraction has been permitted, the whole of the incorrect dose must be discharged before the device can be correctly set. Secondly, by automatically retracting the pawl in readiness for the next dose, the device is put into a "cocked" condition, which means that a user can operate the device accidentally. Thirdly, we have found that where the user is weak he may not depress the push button or trigger completely or smoothly. This may allow the pawl to retract partially or completely before it has reached the full extent of its forward travel. It will therefore appear to the user that the full dose has not been administered and he will then continue to depress the push button or trigger for its full travel. As a result, the user may administer an overdose, which could be fatal.

GB Specification No. 21096904 A describes a dispensing mechanism in which the plunger has an external screw thread and fits within an internally screw threaded fixed sleeve. The plunger is rotated by a drive cap so as to move the plunger axially. The cap incorporates a pawl and ratchet mechanism so that the cap can be rotated in one direction without rotating the plunger, but rotates the plunger in the opposite direction. The volume of fluid to be dispensed in set by rotating the cap in the first direction the desired amount from a zero point. The dose is dispensed by rotating the cap in the opposite direction back to the zero. Whilst this device is not automatically returned to the "cocked" position after each use, it is cumbersome to use, especially when the user is injecting fluid single handedly into his posterior. Furthermore, since the drive between the cap and the plunger is not fully disengaged, the device can be pumped by repeated rotation and contra-rotation of the cap. It has been proposed in PCT Published Application No. WO 85/02546 to operate a syringe using an electric stepper motor to advance the plunger in the syringe a predetermined amount. This may reduce the risk that an incorrect or excessive dose is dispensed, but such a device is expensive and cumbersome and is not suited for carriage upon the person or for general use.

It has further been proposed, for example in Swiss Patent No. 293302 and U.S. Pat. No. 2695023, to use an automatically engaging latch to limit the travel of the plunger of a syringe to the distance between adjacent notches on the plunger into which the latch engages. This permits the user to dispense only single doses. Where multiple doses are required, the user must repeatedly actuate the latch and must count and remember the number of times he has actuated the latch. This is awkward and often a user cannot remember correctly the number of times he has operated the latch, leading to inaccurate doses.

A further problem with the above devices is that a user cannot determine accurately how much insulin or other medicament is left in the body of the syringe or cartridge and hence whether he can achieve the next dosage completely from that syringe or cartridge or whether he must use a fresh one to achieve the complete dose. Mere visual inspection through the transparent wall of the container is usually too inaccurate to be able to distinguish between, say, 8 and 14 units of insulin remaining in the container and some more accurate guide is required.

As a result, a need still exists for a simple measured dose dispensing device which can deliver accurately controlled but variable doses of fluid and which can be used single handedly by weak or infirm users without the risk of "pumping" the device to administer an overdose.

SUMMARY OF THE INVENTION

Accordingly, the present invention provides a hand portable device for dispensing a fluid from a container by means of the axial movement of a piston within the container under the influence of a plunger moved by the device, which device is adapted to receive the container at its forward end and to move the plunger axially forward toward or within the container so as to dispense a selected amount of fluid from the container upon each actuation of the device, characterised in that the device comprises:

i. a disengageable drive mechanism adapted to be reciprocated substantially co-axially of the device and adapted to positively engage the plunger whereby the plunger can be moved axially forward by the drive mechanism and adapted to be disengaged from the plunger to permit relative axial movement between the drive mechanism and the plunger;

ii. a disengagement means for selectively engaging and/or disengaging the drive mechanism from the plunger;

iii. an actuation means, which may be integral with or separate from the disengaging means, for actuating the disengagement means, which actuation means requires a positive operation from a user of the device to engage and/or disengage the drive mechanism from the plunger; and iv. means for selecting the extent of travel of the drive mechanism so as to control the extent of axial movement of the plunger upon actuation of the device.

The device of the invention reduces many of the problems associated with designs proposed hitherto by using a drive mechanism which can be disengaged from the plunger at any point during its travel, notably for the dose selection step. This allows errors in the dose selection to be corrected before the drive is re-engaged. The drive mechanism is locked onto the plunger for the forward stroke of the mechanism, so that the plunger or drive mechanism cannot be partially retracted during the forward stroke, which reduces the risk of administering an overdose. The engagement and/or disengagement of the drive mechanism requires a positive operation to be carried out by the user, so that the device can be left in the de-activated state until the next dose is required and cannot be operated until the positive drive engagement operation has been carried out. However, once the dosage has been selected and the drive has been re-engaged, the device can readily be used single handedly, notably when a dose is being injected into the user's posterior.

The container upon which the device of the invention is to be used can be a conventional syringe body, but is preferably a generally cylindrical cartridge containing the fluid to be dispensed. As indicated above, the invention is of especial use in the self-administration of a medicament, notably insulin, by a user. For convenience, the invention will be described hereinafter in terms of this use.

The medicament is preferably contained in a cartridge, notably one with a comparatively short wide body, typically from 0.3 to 3 cms external diameter and from 3 to 7.5 cms long. The cartridge has one end closed by a transverse membrane or wall, the other being closed by the axially moveable piston. If desired, the one end can carry a hypodermic needle or the like already in position, or this can be provided as a separate component which is secured in place when the cartridge is mounted on the device of the invention. For convenience, the invention will be described hereinafter in terms of the use of a cartridge of insulin.

The cartridge may be mounted at the forward end of the device by any suitable means, for example as a push, screw, bayonet or other fit within an axial socket at the forward end of the device. The socket can contain other components of the device which are to co-operate with the cartridge, for example a mechanism for preventing the plunger from moving rearwardly as described later. It is particularly preferred to provide an internal circumferential annular shoulder or series of projections which act as a stop against which the rim of the cartridge seats when fully home in the socket, thus correctly positioning the cartridge axially in the device.

The cartridge is preferably mounted within a detachable housing which is a screw or other fit into the device, for example into the axial socket. The use of such a housing aids correct mounting of replacement cartridges in the device. By making the housing from a clear plastic material, a user can readily observe the movement of the piston within the cartridge and can assess the amount of fluid in the cartridge. The housing also provides a measure of protection to the cartridge, both physical and against pathogenic organisms and other possible contamination.

Where such a housing is used, the needle end of the cartridge can project through a terminal aperture in the housing or that end of the housing can be closed and can carry a needle or other outlet integrally therewith which projects axially inwardly into the housing to penetrate the membrane at the end of the cartridge.

The cartridge houses the piston which is to be moved by the plunger. This piston can be of conventional design and will usually form part of the cartridge as commercially available. The plunger acts on the piston and the piston can carry a socket or other recess to receive and locate the head of the plunger. In some cases, the plunger can be affixed to the piston and will form part of the cartridge as supplied, in which case the plunger will extend into the device when the cartridge is mounted on the device. However, it is preferred that the plunger form part of the device rather than of the cartridge and, for convenience, the invention will hereinafter be described with respect to this configuration.

The device typically comprises a substantially cylindrical hollow housing containing the various mechanisms of the device as described below assembled substantially co-axially around the plunger.

The plunger is preferably a simple elongated rod which extends axially along the longitudinal axis of the device and can have a substantially circular, polygonal, squared or other cross-section as desired. Thus, the plunger may have two or more opposed flatted faces and/or can have two, or more axial grooves in its surface to assist angular location of the plunger with respect to the other components.

The plunger can have a plain surface onto which the drive mechanism acts by a frictional grasp, as when a Torrington type mechanism is used. However, it is preferred that the plunger carry an axial series of transverse ribs, grooves or teeth which engage with corresponding teeth carried by the drive mechanism. The teeth can extend for substantially the full length of the plunger, but this need not be the case and the terminal portions of the plunger can have a plain surface. Preferably, the teeth are of a saw tooth form with the scarp or undercut face of the tooth facing rearwardly. It is preferred that the axial distance between adjacent teeth corresponds to the distance the piston is to move in the cartridge to dispense a unit dose, for example 1 or 2 IUs, of insulin.

The drive mechanism for present use is one which can be completely disengaged from the plunger to permit relative axial movement between them and so that there can be no drive between the drive mechanism and the plunger until the drive is positively re-engaged. However, when the drive mechanism is engaged, it locks onto the plunger so that there is substantially no relative movement between them. A suitable drive mechanism may thus incorporate a mechanism which engages and disengages by radial movement, for example a Torrington type drive in which a series of ball or roller bearings are carried in a tapered cup around the plunger. A plug member can be moved axially into the taper to drive the balls further into the taper and thus radially inwardly to clamp onto the plunger.

However, a particularly preferred drive mechanism comprises two or more jaws arranged substantially symmetrically around the plunger and which can be moved radially inwardly to clamp onto the plunger. The radially inward faces of the jaws preferably carry teeth which co-operate with those carried by the plunger to provide a positive locked drive between the drive mechanism and the plunger when the drive is engaged. The teeth on the jaws preferably have a similar shape to those on the plunger so that there is a positive fit between them.

The jaws or other mechanism for making the positive drive connection between the drive mechanism and the plunger are preferably carried on a split collet type of structure so that they are journalled upon the plunger and can move axially thereon when disengaged. The jaws are normally urged apart by a compression spring or other bias means acting radially outwardly so that they adopt the disengaged position. In a preferred construction, the jaws extend transversely to either side of the plunger and a transverse coil compression spring is held between the jaw extensions at each side of the plunger. The springs can be held within a retaining extensible saddle piece formed integrally with each jaw extension for ease of assembly of the jaw mechanism. Alternatively, the jaws can be carried via leaf spring mountings from the collet or from another part of the drive mechanism.

Means are provided whereby a user can move the drive mechanism axially to set the dose required and to drive the plunger forward. Preferably, the forward drive is by means of a button or the like operatively associated with the plunger and extending axially from the rear end of the device, but others forms of forward drive means can be used. For example, the drive mechanism or a part operatively associated therewith can carry a radial arm which extends through an axial slot in the housing of the device, or a screw type mechanism can be used.

However, a particularly preferred form of drive mechanism comprises the radially moveable jaws described above carried by a split collet assembly journalled on the plunger and having springs or other bias means for urging the jaws radially outwards. The collet or the rear faces of the jaws themselves are acted on by an axially reciprocateable push sleeve journalled upon the plunger. The push sleeve extends rearwardly to provide a push button mounting projecting from the rear of the device so that depression of the button causes the push sleeve and hence the jaws to move axially to drive the plunger forward. If desired, the push button or push sleeve can be recessed within the terminal portion of the housing so that a user must insert some implement, for example a removable nose cap protecting the needle of the cartridge, to be able to operate the forward drive.

The drive mechanism is engaged or disengaged by some means which requires a positive operation by the user of the device so that the drive cannot be accidentally actuated or over-ridden. Thus, where the plunger has two or more flatted surfaces, these can be inset radially from the non-flatted surfaces so that the teeth on the jaws, or the balls in a Torrington type drive coupling as described above, would not engage the flatted surfaces. The drive can therefore be disengaged by rotating the jaws or a part operatively associated therewith, for example the push sleeve described above, to align the jaws with the flatted faces, or vice versa, by a tangential movement. In this position the drive mechanism is disengaged and can move relative to the plunger, for example when it is desired to set the dosage to be dispensed. The positive operation required by the user is to rotate the push sleeve or the protruding push button connected thereto with respect to the drive mechanism and this action has to be reversed before the drive can be re-engaged.

However, a preferred form of disengagement mechanism is a cam or other radially acting mechanism which moves the drive mechanism radially in and out of engagement with the plunger. Thus, the opposed jaws described above can be moved in and out by a cam carried internally on a rotating sleeve portion of the housing within which the operating mechanism of the device is housed. In this case, the rotatable sleeve section provides both the disengagement means (the internal cams) and the actuation means (the section of the housing itself carrying the cams) in a single member.

The cams acts against the spring or other bias holding the jaws clear of the plunger and brings the jaws into engagement with the plunger. The cams also retain the jaws in the engaged position, thus locking the drive connection between the drive mechanism and the plunger, until the cams are released by rotating the sleeve section carrying them. Alternatively, the jaws can be tied to the cams so that they are moved radially in both directions by the cams without the need for a spring bias. A further form of drive disengagement and actuation mechanism is an axial or tangentially mounted lever which is mounted by means of a pivot within the wall of the housing. Raising one end of the lever causes the other end to bear radially against the jaws or other radially moveable component of the drive mechanism either directly or via an intermediate component so as to urge them radially inward and into engagement with the plunger.

Where a rotatable cammed housing section is used, it is preferred that the exterior of this section carry markings or have an oval cross-section so that a user can tell the orientation of the section simply by touch.

The device incorporates a dosage selection mechanism for selecting the extent of axial travel of the disengaged drive mechanism so as to control the movement of the plunger and hence the volume of fluid discharged from the cartridge. The drive is then re-engaged and the drive mechanism returned to the datum point carrying the plunger with it. In this way the plunger moves an amount which is set by the extent to which the drive mechanism is retracted from a datum point. Since the drive is disengaged during the retraction of the drive mechanism, it is possible to correct any over- or undershoot in the movement of the drive mechanism before the drive is re-engaged. Also, once the drive has been re-engaged, due to the fact that the plunger does not readily move rearwardly, as described below, the user cannot retract the drive mechanism or the plunger without positively disengaging the drive again. Hence tremulous or jerky operation of the device will not affect the dose to be dispensed.

The datum point for the dosage setting mechanism is preferably a stop determining the extent of forward travel of the drive mechanism or a part operationally associated therewith. Thus, the abutment of the push button driving the push sleeve against the end of the housing can provide that datum point. However, it is preferred that the datum point be provided by a stop located within the device against which the front face of the drive mechanism buts at the forward extreme of its travel. Conveniently, this stop is also the stop against which the rim of the cartridge seats when it is fitted to the device, so that the stop serves as the datum point both for positioning the cartridge to one side and for the dosage selection mechanism on the other.

The dosage selection means can operate axially, as when the push sleeve engaging the jaws described carries one or more external radial projections which but against co-operating projections carried by the housing within which the sleeve reciprocates. Rotation of the housing selects which stops will engage and hence the length of travel of the drive mechanism. Alternatively, the dosage selection mechanism can take the form of a side arm carried by the push sleeve and protruding through a stepped track or aperture in the wall of the housing which allows the sleeve to be retracted for the full length of one axial section of the track. The sleeve or a part operatively associated therewith then has to be rotated to allow the arm to move transversely into the next section where a larger dose is required.

However, we have found that a screw mechanism provides a particularly effective and accurate means for retracting the drive mechanism. Thus, for example, the dosage selection means utilises a screw sleeve journalled upon the push sleeve. The screw sleeve carries an external projection or screw thread which co-operates with an internal screw thread on the housing wall. Alternatively, the screw sleeve can have a radial projection which is journalled in a helical track or aperture in the wall of the housing of the device, or vice versa.

The screw thread can have any suitable pitch having regard to the axial movement required to achieve the minimum dose to be administered. The optimum pitch can readily be determined by simple trial and error having regard to the geometry of the device, for example so that ⅛th of a turn of the screw sleeve achieves an axial travel corresponding to the axial distance between adjacent teeth on the plunger.

The screw sleeve has means by which it can be rotated by the user, for example by means of a pin or arm projecting through the wall of the device; or preferably by a collar located adjacent the end of the housing. This is connected to the sleeve through a spline coupling or the like to allow relative axial movement between the collar and the sleeve.

The forward movement of the plunger may be achieved by returning the dosage selection mechanism, for example the screw sleeve, to the datum point when the drive is re-engaged. However, this may not be easy or convenient, notably where this requires the user to rotate part of the device to achieve this, and it is preferred to employ an axial push action, e.g. by means of the push sleeve as described above. We therefore prefer that the dosage selection mechanism be demountably connected to the drive mechanism so that, when the drive is re-engaged, the connection between the dosage selection and the drive mechanisms is released. This can be conveniently achieved by providing a latch mechanism at or adjacent the forward end of the dosage selection mechanism, e.g. the screw sleeve, which latch mechanism engages the drive mechanism when the latter is in the disengaged position but which releases the drive mechanism when the latter is in the engaged position. The drive mechanism can then be driven forward independently of the dosage selection mechanism. Suitable latch mechanisms can readily be devised having regard to the specific design of the device they are to fit.

The device also comprises means whereby the dosage corresponding to a selected extent of retraction of the drive mechanism can be observed aurally or visually by a user, for example by means of a clicker mechanism. Preferably, the push sleeve or the screw sleeve carries markings correlating the dosage with the extent of axial movement. Where a screw sleeve is used, the markings are carried along a spiral path and are progressively brought into register with a window or port in the wall of the housing so that the user can see what dose is to be dispensed.

In order that a user can determine whether or not sufficient fluid remains within the container to achieve a stated amount to be dispensed, it is preferred to provide a second stop means carried by the plunger, for example at the rearward end thereof, which is engaged by the drive mechanism or push member as it is retracted. The second stop will prevent the drive mechanism or push member from being withdrawn to its full extent if the residual potential travel of the plunger is less than the desired dose. A user will detect resistance to operation of the dosage selection mechanism or will notice when the spline drive between collar 10 and the screw sleeve is over-ridden when this occurs. The user can then tell from the dose indicated as described above whether there is sufficient medicament in the cartridge to complete the required dose.

As indicated above, the plunger should not be free to move rearwardly during normal use of the device. This can be achieved by ensuring that the plunger is a frictional fit within the device. However, this may require excessive force to operate the device if the frictional forces are to overcome attempts to retract the plunger when the drive mechanism is engaged. We therefore prefer to provide some form of one way device to provide positive means for preventing the plunger from moving rearwardly when a cartridge is mounted on the device. Conveniently, this means takes the form of a second pawl arrangement which engages with the teeth on the plunger shank at the forward end of the device. Whilst this pawl can be permanently engaged, it is preferred that it be is biassed so as to be disengaged from the plunger when no cartridge is in position. This enables the plunger to be retracted when a cartridge has been removed from the device so that a new one can be fitted. When the cartridge is mounted on the device, it or its housing causes the second pawl to re-engage with the teeth on the plunger.

The device of the invention can be provided with other features to enhance its use. For example, the device can be put up in the form of a pen type object with a cap over the needle end of the device and a clip for mounting it in the pocket of the user.

From the above, it will be seen that from one aspect, the present invention provides a device for dispensing a controlled amount of fluid from a container, which device comprises an assembly adapted to be mounted upon a container in which a plunger is adapted to be moved axially along the container in increments so as to drive a piston within the container and thus to dispense fluid from the container, characterised in that the assembly comprises a drive mechanism adapted to be reciprocated axially of the device and to be positively engaged with the plunger for the forward stroke of the drive mechanism so as to prevent relative movement between the plunger and the drive mechanism and to move the plunger forward in the container, which drive mechanism requires a positive action to disengage it from the plunger so as to permit relative movement of the plunger and drive mechanism for at least rearward movement of the drive mechanism; in that the forward travel of the drive mechanism is limited by a fixed stop mechanism; and in that the extent of the forward stroke of the drive mechanism is selected by withdrawing the drive mechanism a selected distance from the said fixed stop.

From a preferred aspect, the invention provides a device for dispensing a controlled amount of fluid from a container by means of a piston journalled in said container, which device is characterised in that it comprises:

a. an elongated generally cylindrical hollow body member having its forward end adapted to receive and retain the fluid container;

b. a plunger extending axially within said body member and adapted to be moved axially in a series of individually selected increments and to bear against the piston within the container when mounted on the said body member so as to move the said piston to dispense doses of fluid from the container at each incremental movement of the plunger;

c. a radially acting jaw member adapted to be moved into engagement with the said plunger to provide a positive drive connection between said jaw and said plunger, and to be disengaged from said plunger so as to permit relative axial movement between said plunger and said jaw;

d. means requiring positive operation by a user of the device for engaging or disengaging said jaw from said plunger.

e. an axially acting push sleeve journalled upon said plunger for moving said jaw forward when engaged to said plunger;

f. axially acting dosage selection means comprising a screw thread moved sleeve journalled for axial movement upon said push sleeve and carrying demountable means for engaging said jaw when said latter is disengaged from said plunger and for moving it rearwardly from a datum point so as to select the possible extent of forward travel of said plunger and to release said jaw when said jaw is re-engaged with said plunger for axial movement by said push sleeve; and g. means for rotating said screw sleeve so as to select the extent of rearward movement of said screw sleeve from said datum point.

The invention also provides a device of the invention having mounted thereon a container, notably a cartridge, containing a medicament; and a medicament cartridge for use with the device, notably one housed within a housing adapted to be secured to the front end of the device of the invention.

The invention yet further provides a method for administering a fluid medicament to a patient using a device of the invention.

DESCRIPTION OF THE DRAWINGS

The device of the invention will now be described by way of illustration with respect to a preferred form thereof as shown in the accompanying drawings in which.

DESCRIPTION OF A PREFERRED EMBODIMENT OF THE INVENTION

Figure 1:
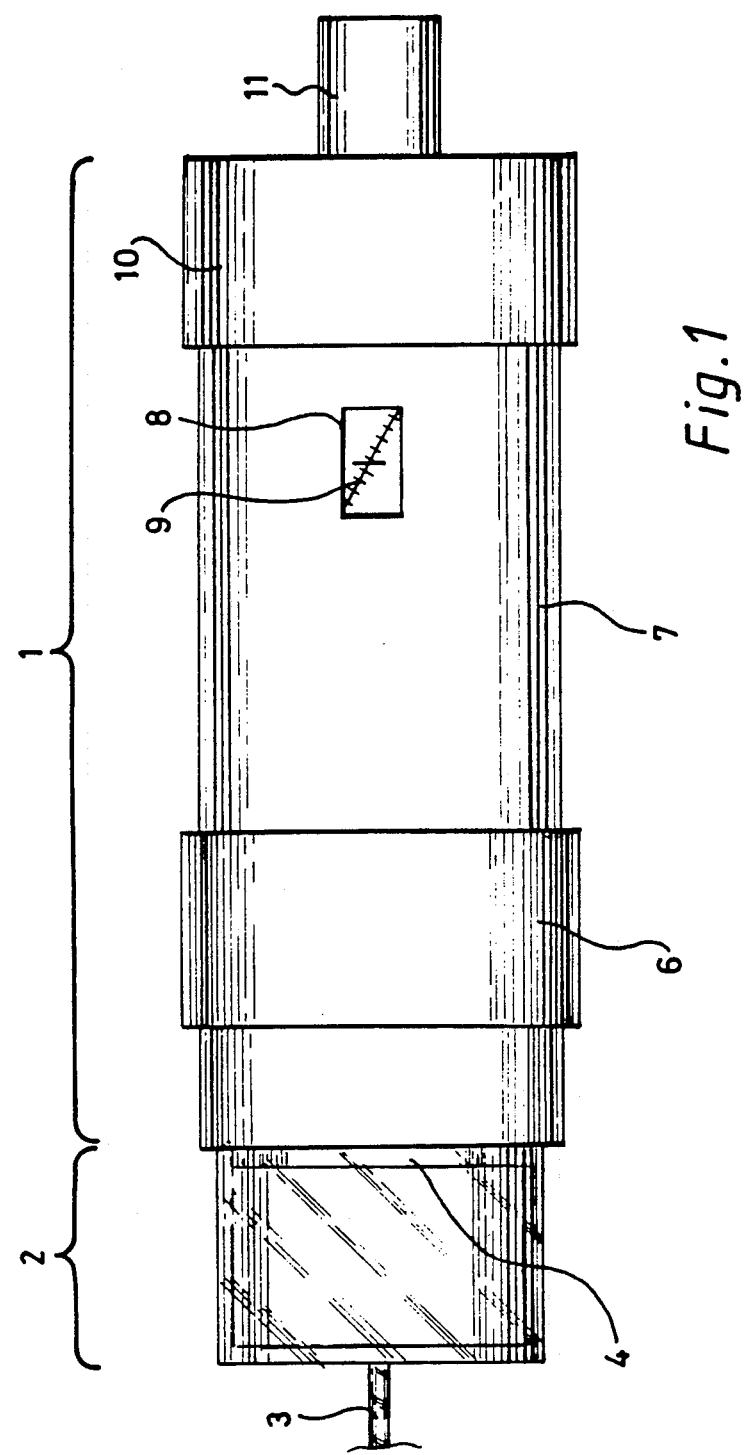
FIG. 1 is an overall external diagrammatic view of the device.

The device comprise an elongated generally cylindrical housing 1 having an axial socket at one end into which a generally cylindrical cartridge 2 can be screw or push fitted. The cartridge typically has a cylindrical clear plastics or glass barrel with a hypodermic needle 3 protruding substantially co-axially from the free end thereof. A piston 4 journalled within the cartridge 2 is incrementally moved by a plunger 5 extending substantially co-axially rearwardly into the housing 1 of the device. The plunger 5 is separate from the piston and forms part of the device of the invention.

Figure 3:
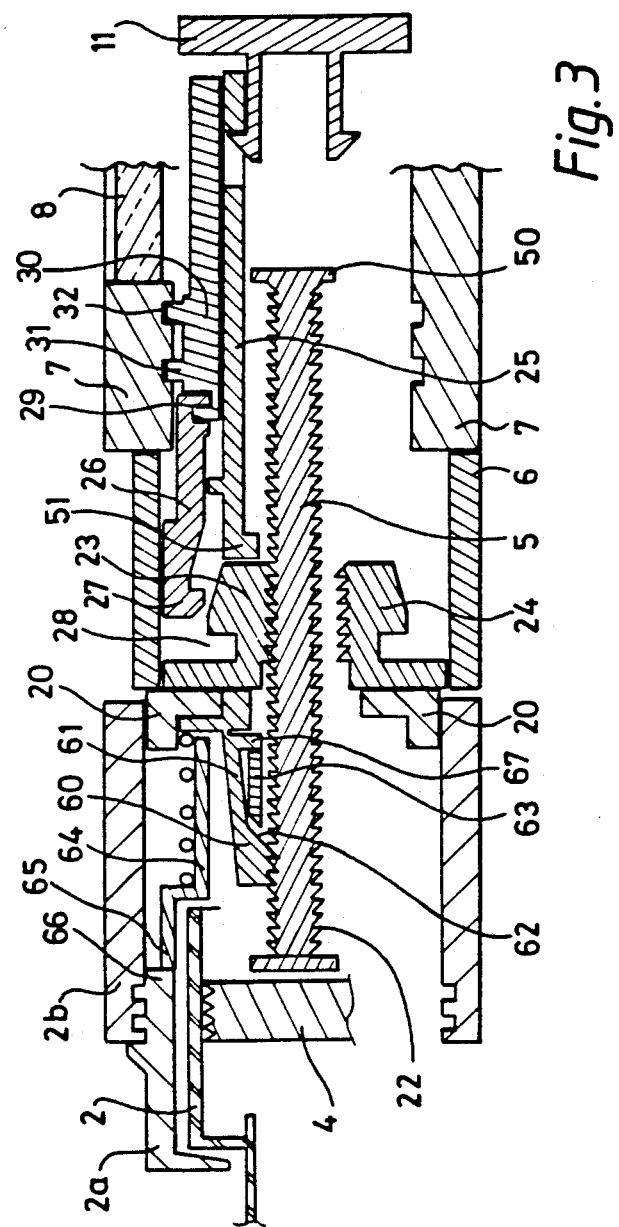
FIG. 3 is a cross-sectional diagrammatic view through an alternative form of the device showing some of the components in greater detail.

As shown in FIG. 3, the cartridge 2 can be housed in a housing 2a which is a screw fit into a collar 2b extending axially from the front end of the housing 1.

The rim of the cartridge seats against a circumferential radial shoulder or series of radial projections 20 carried internally by the housing 1 so as to locate the cartridge at a consistently fixed position with respect to the dosage selection mechanism as described below.

The device is provided with a pawl type one way mechanism which engages teeth on the plunger so as to prevent rearward movement of the plunger 5 once the cartridge is in place. This one way mechanism is shown diagrammatically as 21 in FIG. 2 and is biassed to retract radially when the cartridge is removed. For example, the housing can incorporate a twist mechanism which both locks the cartridge in position and actuates the one way mechanism; or the rim of the end of the cartridge or its housing can bear against part of the one way mechanism as it seats home to actuate the one way mechanism. The one way mechanism disengages when the cartridge is removed to allow the plunger 5 to be retracted into the device to permit a new cartridge to be mounted on the device.

A preferred form of the one way mechanism 21 is shown in FIG. 3 and comprises a pair of diametrically opposed pawls 60 carried on spring arms 61 snap fitted onto the annular shoulder 20 to extend forward of the shoulder into the axial socket in which the cartridge is mounted. The pawls 60 have an inclined rearward face 62 which bears against a correspondingly angled face carried by a split collet 63 mounted around the plunger shank and radially inward of arms 61. The collet is attached to a spring loaded sleeve 64 which is a slideable fit within the socket and is spring biassed into its forward position. The front end of the sleeve 64 provides a stop 65 against which the rim 66 of the housing 2a bears as it is mounted in the device. This causes the sleeve 64 to be moved axially rearwardly to carry the inclined face of collet 63 clear of the inclined face 62 of the pawl and to bring the rear edge of collet 63 into contact with a stop 67 carried on the radially inward face of are 61. This causes the arm 61 to flex radially inward and urge pawl 60 into engagement with the teeth on the plunger. When the housing 2a is removed to fit a new cartridge 2, this allows the sleeve 64 to move forward under the thrust of the spring so that collet 63 moves forward to release stop 67 and bears against the inclined face 62 to lift the pawl 60 clear of the teeth on the plunger. The plunger can now be retracted into the device to enable another cartridge to be fitted. By using the rear of the accurately moulded housing 2a to actuate the pawl mechanism 60-67, rather than the rim of the cartridge 2, variations in the size of the cartridge can be accomodated.

Rearwardly of shoulder 20, the body of the device houses the plunger drive mechanism, the means for engaging and disengaging the drive mechanism from the plunger and the dosage selection means. In the form of the device shown, these take the form of a series of members concentrically journalled around the plunger 5.

As shown, the housing comprises a rotatable section 6 which houses the drive engagement mechanism; a fixed section 7 containing the dosage selection mechanism and having a port 8 through which a scale 9 indicating the dose selected can be seen by the user; a further rotatable collar or sleeve 10 for operating the dosage selection mechanism; and a terminal axially operating push button 11 for driving the plunger forward to dispense the selected dose. The various sections of the housing can have any desired external shape, but it is preferred that the housing 1, sleeve 6 and section 7 have an oval external cross-section so that the relative rotational position of one with respect to the other can readily be detected by a user, notably by a blind person.

Figure 4:
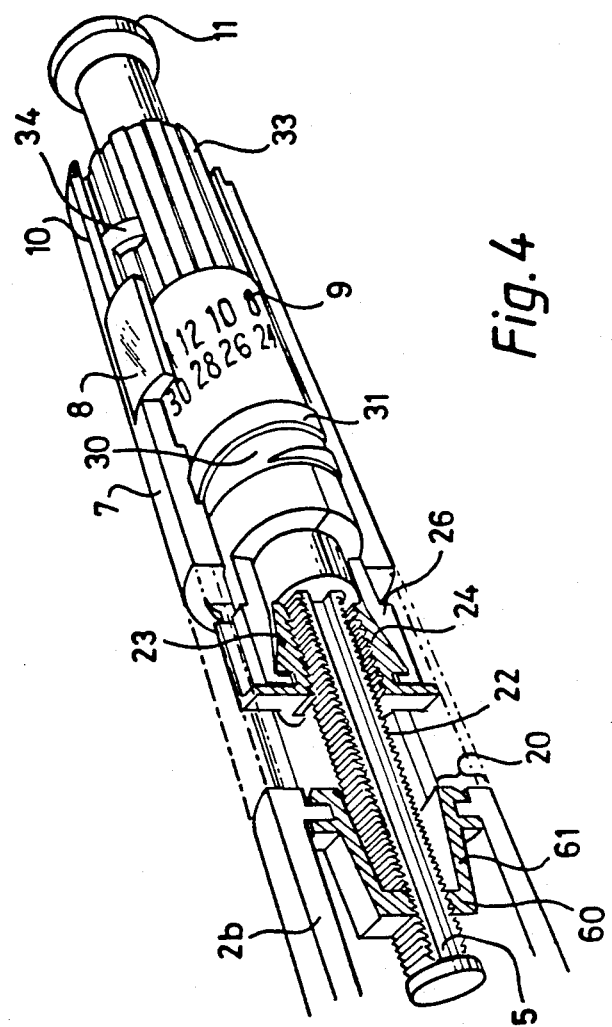
FIG. 4 is a part cut away/part perspective view of the device.

The plunger 5 preferably has a substantially circular cross-section, but can have a squared, triangular or other cross-section shape if desired. For example, as shown in FIG. 4, it may have two opposed flats along its length to guide the drive means.

The plunger 5 carries a series of circumferential ribs or teeth 22 which form an axial ratchet into which the one way mechanism 21 and the radially clampable drive mechanism described below engage. The teeth 22 are of a saw tooth form with the scarp face of the teeth directed rearwardly. Preferably, the teeth extend axially for the full length of the plunger 5. As indicated above, it is preferred that the axial distance from one tooth to the next corresponds to a dosage unit for the material being dispensed.

Located to the rear of shoulder 20 is the drive mechanism and the mechanism for engaging and disengaging this from the plunger. The drive mechanism is a pawl type mechanism which is radially engageable and disengageable with the teeth on the plunger and comprises two jaws 23 and 24 diametrically opposed to one another and carrying on their radially inward faces teeth which correspond to and engage with the teeth 22 on the plunger.

Figure 2:
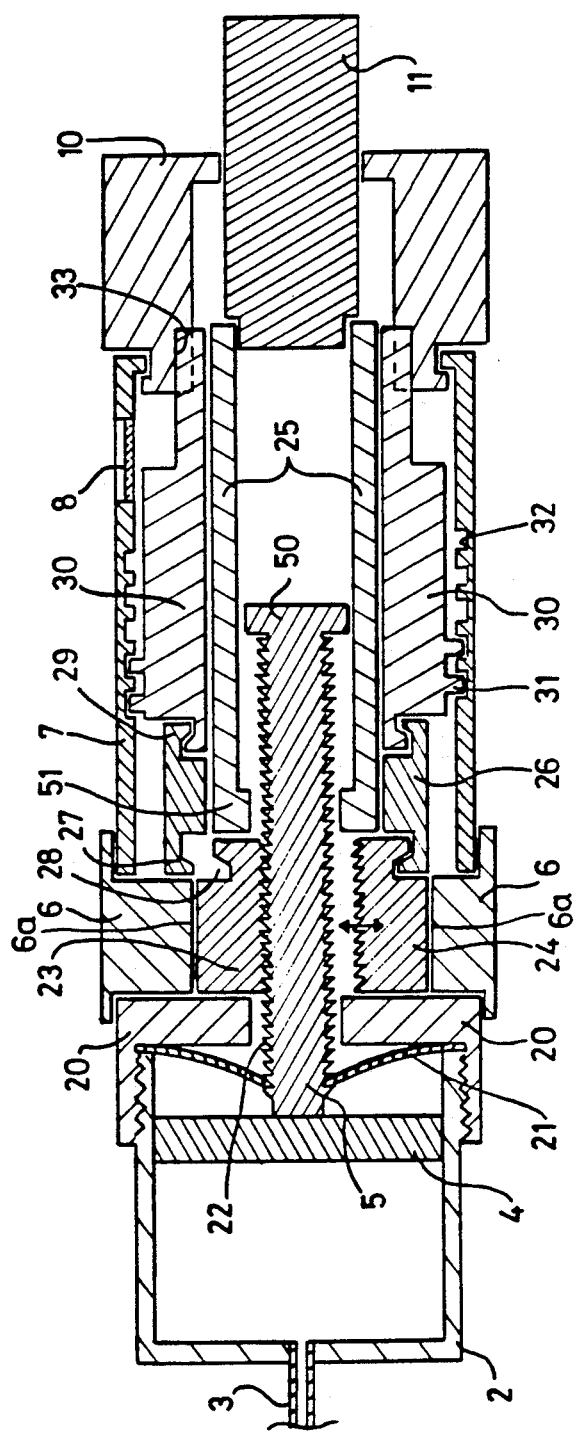
FIG. 2 is a cross-sectional diagrammatic view through the device of FIG. 1.

The jaws are normally urged radially outwardly, as shown for jaw 24 in FIGS. 2 and 3, by transverse coil springs acting between the jaws 23 and 24 or by other bias means (not shown) so that their teeth do not engage those of the plunger, which is then free to move axially with respect to the jaws when they are in their outward position, but is locked to the jaws when they are in their radially inward position, as shown for jaw 23 in FIGS. 2 and 3.

The jaws are moved radially inward against the thrust of the coil springs by a pair of cams 6a carried on the internal face of the rotatable section 6 of the housing or formed by the narrower diameter sectors of the oval cross-section of the rotatable section 6. The user has to twist section 6 to engage or disengage the jaws from plunger 5 and thus engage or disengage the drive to the plunger. If desired, section 6 can be spring biassed towards the drive disengaging position so that the user always has to twist section 6 before the device can be used.

The shoulder 20, as shown in FIGS. 2 and 3, defines the forward limit of the travel of the drive mechanism and provides the datum point from which the dosage is determined. In the device shown in FIGS. 2, 3 and 4, the forward faces of jaws 23 and 24 but against the rear face of shoulder 20 to set the zero or datum point for the dosage selection mechanism.

A push sleeve 25, journalled on plunger 5 and within the dosage selection mechanism described below, acts axially on the rear faces of the jaws 23 and 24 when in their drive engaged position to drive the jaws and hence the plunger 5 forward. When the jaws are in the drive disengaged position, they still bear against the push sleeve so that they carry it axially rearwards with them during the dosage selection. The push sleeve 25 provides the mechanical link between the terminal push button 11 which a user presses and the jaws 23 and 24.

The jaws 23 and 24 are moved axially by means of a split jaw drive sleeve 26 which has forward hooks 27 which engage similar recesses 28 at the rear of the jaws and rearward hooks 29 or other flexible linkages which connect the sleeve 26 axially to the forward end of the screw sleeve 30 of the dosage selection mechanism. When the jaws are in the drive disengaged position as shown for jaw 24 in FIGS. 2 and 3, the hooks 27 and recesses 28 are engaged and the jaws can be moved axially with the screw sleeve 30. When the jaws are in the drive engaged position, as shown for jaw 23 in FIGS. 2 and 3, the hooks 27 are released from recesses 28 to permit the jaws to move axially with sleeve 25 and free from the screw sleeve 30 (as shown in FIG. 3).

The dosage selection mechanism is housed within section 7 of the housing and comprises a screw sleeve 30 journalled for rotation and axial movement upon push sleeve 25. Sleeve 30 carries an external screw thread 31 which engages a similar thread 32 carried internally by section 7 of the body of the device. Sleeve 30 is rotated and thus caused to move axially by means of collar 10 driving the sleeve through a spined drive 33 shown in FIGS. 2 and 3. Collar 10 or the window insert in port 8 preferably has a ratchet or clicker mechanism 34 to give an audible indication as the dose is selected.

Retraction of sleeve 30 carries the jaw drive sleeve 26 and the jaws 23 and 24 with it when they are in the disengaged position and the dose selected can be seen through port 8. Re-engagement of jaws 23 and 24 with the plunger, breaks the latch 27/28 and allows the push sleeve 25 and the jaws 23 and 24 to move independently of the screw sleeve 30 and the jaw drive sleeve 26.

To indicate when there is insufficient fluid left in the cartridge to achieve the next dose, a radial shoulder or stop 50 is located at or adjacent the rearward end of plunger 5. This co-operates with a corresponding stop or shoulder 51 at the forward end of the push sleeve 25. The stops engage when the push sleeve is retracted to the maximum extent possible as the plunger 5 approaches the extreme of its forward travel. The user can then see from the dose displayed at the port 8 whether the cartridge contains the requisite amount of fluid. Since the plunger drive is not engaged at this time, the user can then set the dosage mechanism to the required dose if this is less than the amount indicated as remaining in the cartridge without having to discharge fluid as with a conventional device.

Push sleeve 25 is provided with a push button end cap 11 protruding axially from the body of the device which the user depresses to drive the sleeve 25 forward within the housing until the front faces of jaws 23 and 24 but against the rear of shoulder 20. The jaws 23 and 24 can only be moved rearwardly when they have been disengaged from the teeth 22 on the plunger 5, since the one way mechanism 21 will prevent rearward movement of the plunger 5. If a user attempts to set the dosage mechanism whilst the drive is engaged, he will detect resistance to rotation of sleeve 10. If he ignores this, the spline drive 33 between collar 10 and the screw sleeve 30 will be over-ridden to release the screw sleeve to prevent damage to the mechanism. However, unless the drive is engaged, depression of button 11 will not achieve any forward movement of the jaws or discharge of fluid from the cartridge 2.

The above device can be manufactured in many suitable materials and readily lends itself to manufacture by injection moulding of suitable plastics materials with the various components being snap fits upon one another.

In operation, a user rotates the sleeve 6 to disengage the drive mechanism. Jaws 23 and 24 should be seated against the rear face of shoulder 20, the zero setting, from the previous use of the device, but the screw sleeve 30 will be at the dosage position previously selected. The user can thus see what dose was last administered where a sequence of different doses has to be administered. Sleeve 10 is rotated, say clockwise, to bring sleeve 30 to its forward position at which the latching mechanism 27/28 engages the jaws 23 and 24 and seats them firmly against the rear face of stop 20. The engagement of the latches can be used to provide an audible signal when this occurs, or the resistance to further forward movement will provide the signal to the user that the zero setting has been reached. The dosage displayed through port 8 will now read zero.

Sleeve 10 is then rotated anti-clockwise the desired number of turns, as evidenced by the number of clicks heard or by the dose displayed at the port 8, to retract screw sleeve 30, the jaw drive sleeve 26 and the jaws 23 and 24 and the push sleeve 25 the desired distance with respect to plunger 5. This will also cause the push button 11 to be extended from the rear end of the device.

Sleeve 6 is then rotated to re-engage the positive drive between the push sleeve 25, the jaws 23 and 24 and the plunger 5. This action will also disengage the latch 27/28 between jaws 23 and 24 and the jaw drive sleeve 26. At this point the device is cocked .nd ready to dispense the desired dose from the cartridge. However, the device has required a series of positive actions to achieve this state and would not normally be retained by a user in the cocked state, but would be stored with the drive disengaged so that accidental actuation of the device can not occur.

The user then inserts the point of needle 3 into his arm, buttock or other suitable point in his body and depresses button 11 to administer the dose of insulin. The dose is administered by depressing the button fully. If the button is not depressed fully, the user can detect this and can complete the dose administration. If desired, a coloured band can be mounted around button 11 which will remain partially exposed until the button is fully depressed. Release of pressure on button 11 does not allow the plunger 5 to retract as with previous designs, so that jerky or interrupted depression of button 11 does not allow the user to pump the device to administer an excessive dose.

When the full dose has been administered, the jaws 23 and 24 will but against the rear of shoulder 20. Due to the action of the one way mechanism 21, 60–67, the blocks 23 and 24 can not be retracted and administration of a further dose of insulin is not possible until the whole process of dose selection and re-cocking of the device is carried out. The device will therefore resist accidental overdosing due to repeated pressing of button 11.

As stated above, the device of the invention finds use wherever it is desired to provide a measured dose syringe, for example in the administration of Other medicaments or in dispensing accurately known amounts of a fluid, for example in blood teats or analytical work. It will also be appreciated that the device may be altered in ways which do not affect the fundamental operating concept of the device, for example by using a short plunger within the device to drive an intermediate plunger linked to a plunger carried by the piston of the cartridge; or to incorporate a flexible drive between the plunger 5 and the piston 4 so that the device of the invention is mounted at an angle to the axis of the cartridge.

What I claim is:

1. A device for dispensing a controlled amount of fluid from a container, which device comprises an assembly adapted to be mounted upon a container in which a plunger is adapted to be moved axially along the container in increments so as to drive a piston within the container and thus to dispense fluid from the container characterised in that the assembly comprises a drive mechanism adapted to be reciprocated axially of the device and to be positively engaged with the plunger for the forward stroke of the drive mechanism so as to prevent relative movement between the plunger and the drive mechanism and to move the plunger forward in the container, which drive mechanism requires a positive action to disengage it from the plunger so as to permit relative movement of the plunger and drive mechanism for at least rearward movement of the drive mechanism; in that the forward travel of the drive mechanism is limited by a fixed stop mechanism; and in that the extent of the forward stroke of the drive mechanism is selected by withdrawing the drive mechanism a selected distance from the said fixed stop.

2. A device as claimed in claim 1 which comprises:
   a. a hollow body member having one end adapted to receive and retain the fluid container
   b. a plunger carried by said body member and adapted to be moved axially in a series of increments and to bear against the piston within the container so as to move the said piston to dispense doses of fluid from the container at each incremental movement of the plunger
   c. a push member carried by said body member for axial movement with respect to said body member and having means for achieving positive engagement with the said plunger in the forward direction of travel of the push member
   d. means requiring positive operation for releasing said positive engagement and thus permitting relative axial movement between the push member and the plunger in at least the rearward direction of travel of the said push member
   e. a stop means against which the push member or a part associated therewith butts at the extreme of the plunger's forward travel on each of its incremental movements
   f. means for withdrawing the push member or its said associated part axially from the stop means to a selected distance whereby the extent of each incremental forward movement of the plunger can be selected
   g. means for inhibiting rearward movement of the plunger whilst the container is located upon the body member 3. A device as claimed in claim 2 wherein there is provided a second stop means carried by said plunger which is engaged by the drive mechanism as it is retracted whereby the second stop member prevents the drive mechanism from being withdrawn to its full extent if the residual potential travel of the plunger is less than the desired dose.

4. A device as claimed in claim 1 wherein means are provided whereby the inhibition of the rearward movement of the plunger is removed or released when the container is removed from the body member.

5. A device as claimed in claim 4 wherein rearward movement of the plunger is prevented by a ratchet mechanism which is engaged by rotating part of the body member which also locks the container in position.

6. A device as claimed in claim 1 wherein the positive drive between the plunger and the drive mechanism is achieved by means of a radially acting mechanism which engages the shank of the axially reciprocable plunger member.

7. A device as claimed in claim 6 wherein the plunger has a series of ratchet teeth along its outer surface which are engaged directly or indirectly by a radially expansible toothed clamp member carried terminally by a sleeve push member journalled for axial movement within the device.

8. A device as claimed in claim 7 wherein the sleeve member is moveable axially by rotation thereof using a screw thread mechanism.

9. A device as claimed in claim 6 wherein the radially acting mechanism is actuated by rotation of a cam or similar mechanism to drive the radially acting mechanism radially inwardly into engagement with the plunger.

10. A device for administering insulin from a cylindrical cartridge having a piston journalled therein for axial movement along the cartridge to dispense the insulin contents of the cartridge through a needle outlet into the body of a user, which device comprises:
    a. a cylindrical hollow body member having one end adapted to receive and retain the cartridge
    b. a plunger journalled within the said body member and adapted to be moved axially in a series of increments and to bear against the piston within the container so as to move the said piston to dispense discrete and selectable doses of insulin from the cartridge at each incremental movement of the plunger
    c. a generally cylindrical push sleeve journalled within the said body member for axial movement with respect to said body member
    d. a pair of opposed clamp members mounted for radial movement within the said body member and which can be moved radially inwardly to positively engage the said plunger in the forward direction of travel of the push sleeve whereby the plunger is driven forward by the said sleeve, but which can be moved radially outwardly to disengage from the said plunger for the rearward movement of the said sleeve to permit relative axial movement between the push sleeve and the plunger in at least the rearward direction of travel of the said push sleeve
    d. cam means operable from the exterior of the said body member and requiring positive operation for moving the said clamp members radially inward or outward
    e. an inwardly directed shoulder within the body member which acts as a stop means against which the push member or the clamp members but at the extreme of the plunger's forward travel on each of its incremental movements
    f. an external rotatable member co-axial with the said body member for rotating the said sleeve member and causing it to move axially under the influence of a screw thread mechanism co-operating between the said body and the said sleeve whereby the sleeve can be moved rearwardly to a selected extent from the said stop shoulder when the clamp members are disengaged from the said plunger and thereby select tee extent of forward travel of the plunger when the clamp members are re-engaged with the plunger for forward movement thereof.

11. A hand portable device for dispensing a fluid from a container by means of the axial movement of a piston within the container under the influence of a plunger moved by the device, which device is adapted to receive the container at its forward end and to move the plunger axially forward toward the container so as to dispense a selected amount of fluid from the container upon each actuation of the device, characterised in that the device comprises a drive mechanism adapted to be reciprocated axially of the device and to be positively engaged with the plunger for the forward stroke of the drive mechanism so as to prevent relative movement between the plunger and the drive mechanism and to move the plunger forward, which drive mechanism requires a positive action to disengage it from the plunger so as to permit relative movement between the plunger and drive mechanism for at least rearward movement of the drive mechanism; in that the forward travel of the drive mechanism is limited by a fixed stop mechanism; and in that the extent of the forward stroke of the drive mechanism is individually selectable for each actuation of the device by withdrawing the drive mechanism or a part operatively associated, therewith a selected distance from a fixed stop defined by said fixed stop mechanism.

12. A hand portable device for dispensing a fluid from a container by means of the axial movement of a piston within the container under the influence of a plunger moved by the device, which device is adapted to receive the container at its forward end and to move the plunger to dispense a selected amount of fluid from the container upon each actuation of the device, characterised in that the device by axially moving said drive mechanism a selected amount relative to said plunger while said drive mechanism is disengaged therefrom comprises:

i. a disengageable drive mechanism adapted to be reciprocated axially of the device and adapted to positively engage the plunger whereby the plunger can be moved axially forward by the drive mechanism and to be disengaged from the plunger to permit relative axial movement between the drive mechanism and the plunger;
  ii. a disengagement means for selectively engaging or disengaging the drive means from the plunger;
  iii. an actuating means, which may be the integral with or separate from the disengagement means, for actuating the disengagement means, which actuation means requires a positive operation from a user of the device to engage and/or disengage the drive mechanism from the plunger; and
  iv. means for individually selecting the extent of travel of the drive mechanism for each actuation of the device so as to control the extent of axial movement, of the plunger upon actuation of the device.

13. A hand portable device for dispensing a fluid from a container by means of the axial movement of a piston within the container under the influence of a plunger moved by the device, which device is adapted to receive the container on its forward end and to move the plunger axially forward towards or within the container so as to dispense a selected amount of fluid from the container upon each actuation of the device, characterised in that the device comprises:

a. an elongated generally cylindrical hollow body member having its forward end adapted to receive and retain the fluid container;
  b. a plunger extending axially within said body member and adapted to be moved axially in a series of individually selected increments and to bear against the piston within the container when mounted on the said body member so as to move the said piston to dispense doses of fluid from the container at each incremental movement of the plunger;
  c. a radially acting jaw member adapted to be moved into engagement with the said plunger to provide a positive drive connection between said jaw and said plunger, and to be disengaged from said plunger so as to permit relative axial movement between said plunger and said jaw;
  d. means requiring positive operation by a user of the device for engaging or disengaging said jaw from said plunger.
  e. an axially acting push sleeve journalled upon said plunger for moving said jaw forward when engaged to said plunger;
  f. axially acting dosage selection means comprising a screw thread moved sleeve journalled for axial movement upon said push sleeve and carrying demountable means for engaging said jaw when said latter is disengaged from said plunger and for moving it rearwardly from a datum point so as to select the possible extent of forward travel of said plunger and to release said jaw when said jaw is re-engaged with said plunger for axial movement by said push sleeve; and
  g. means for rotating said screw sleeve so as to select the extent of rearward movement of said screw sleeve from said datum point.

14. A device as claimed in claim 11 wherein the plunger carries an axial series of transverse teeth and the drive mechanism carries corresponding teeth adapted to engage the teeth on the plunger when in the drive engaged position.

15. A device as claimed in claim 11 wherein the drive mechanism is actuated by a radially acting cam means which acts to move the mechanism radially inward to engage the plunger and to retain it in engagement with said plunger during forward movement of the plunger.

16. A device as claimed in claim 11 wherein the device is provided with means for positively acting on said plunger so as to prevent rearwards movement of said plunger at all times when a container is mounted on the device.

17. A device as claimed in claim 11 wherein said datum point is provided by a stop means against which a component selected from the drive mechanism and a part operatively associated therewith buts at the extreme of the forward travel of plunger on each of its incremental movements.

18. A device as claimed in claim 11 wherein there is provided a second stop means carried by said plunger which is engaged by a component selected from the drive mechanism and a part operatively asociated therewith as it is retracted, whereby the second stop member prevents the drive mechanism from being withdrawn to its full extent if the residual potential travel of the plunger is less than the desired dose.

19. A device as claimed in claim 11 having a container containing a medicament is mounted at its forward end.

* * * * *